(12) United States Patent
Karanam et al.

(10) Patent No.: US 11,690,579 B2
(45) Date of Patent: Jul. 4, 2023

(54) ATTENTION-DRIVEN IMAGE DOMAIN TRANSLATION

(71) Applicant: Shanghai United Imaging Intelligence Co., LTD., Shanghai (CN)

(72) Inventors: Srikrishna Karanam, Cambridge, MA (US); Ziyan Wu, Cambridge, MA (US); Terrence Chen, Cambridge, MA (US)

(73) Assignee: Shanghai United Imaging Intelligence Co., LTD., Shanghai (CN)

(*) Notice: Subject to any disclaimer, the term of this patent is extended or adjusted under 35 U.S.C. 154(b) by 433 days.

(21) Appl. No.: 16/902,760

(22) Filed: Jun. 16, 2020

(65) Prior Publication Data

US 2021/0386391 A1   Dec. 16, 2021

(51) Int. Cl.
| | |
|---|---|
| *A61B 6/00* | (2006.01) |
| *A61B 6/03* | (2006.01) |
| *G06N 3/084* | (2023.01) |
| *G06F 18/22* | (2023.01) |
| *G06F 18/241* | (2023.01) |
| *G06N 3/045* | (2023.01) |
| *G06V 10/774* | (2022.01) |
| *G06V 10/82* | (2022.01) |
| *G06V 40/16* | (2022.01) |

(52) U.S. Cl.
CPC ............ *A61B 6/032* (2013.01); *A61B 6/5211* (2013.01); *A61B 6/54* (2013.01); *G06F 18/22* (2023.01); *G06F 18/241* (2023.01); *G06N 3/045* (2023.01); *G06N 3/084* (2013.01); *G06V 10/774* (2022.01); *G06V 10/82* (2022.01); *G06V 40/171* (2022.01)

(58) Field of Classification Search
CPC ......... A61B 6/5211; A61B 6/54; A61B 5/055; A61B 6/037; A61B 6/461; A61B 6/466; A61B 6/5205; A61B 6/032; G06K 9/6215; G06K 9/6268; G06K 9/6256; G06N 3/0454; G06N 3/084; G06N 3/08; G06V 2201/03; G06V 10/774; G06V 10/82; G06V 40/171; G06V 10/44; G06T 5/008; G06T 5/50; G16H 30/40
See application file for complete search history.

(56) References Cited

U.S. PATENT DOCUMENTS

| | | | | |
|---|---|---|---|---|
| 4,587,194 | A * | 5/1986 | Adair | G03F 7/002 430/394 |
| 2016/0275249 | A1* | 9/2016 | Lee | G16H 10/65 |
| 2018/0326223 | A1* | 11/2018 | Willcut | A61N 5/107 |

* cited by examiner

*Primary Examiner* — Mekonen T Bekele
(74) *Attorney, Agent, or Firm* — Ziegler IP Law Group LLC

(57) ABSTRACT

An apparatus is configured to receive input image data corresponding to output image data of a first radiology scanner device, translate the input image data into a format corresponding to output image data of a second radiology scanner device and generate an output image corresponding to the translated input image data on a post processing imaging device associated with the first radiology scanner device. Medical images from a new scanner can be translate to look as if they came from a scanner of another vendor.

17 Claims, 8 Drawing Sheets

ATTENTION-DRIVEN IMAGE DOMAIN TRANSLATION

TECHNICAL FIELD

The aspects of the present disclosure relate generally to image translation and more particularly to translating images from one domain to another domain.

BACKGROUND

It is not uncommon for an imaging device produced by one vendor to generate an image with a one style, while the same or similar type of imaging device produced by another vendor produces the image in a different style. Clinicians become accustomed to images of a certain style, which is based on the vendor of the particular type of imaging equipment they are using.

In a hospital setting for example, it is common that scanners, such as computed tomography (CT), magnetic resonance (MR) imaging, and positron emission tomography (PET) scanners from a particular vendor X, are employed in use for long periods of a time. When a new scanner from a different vendor Y is deployed, the perceptual style of the images produced by the new scanner from vendor Y may not be the same as, or will be different from, the perceptual style of images associated with the equipment of vendor X, which is what the clinician is used to. The clinicians in this situation will need to make a transition from the type and style of images they are used to seeing to the type and style of the images from the new equipment. This transition can be cumbersome.

Existing techniques for image domain translation are largely based on Generative Adversarial Networks (GANs). GANs are used in training models that can translate or transform an image with one attribute (e.g. a face with no eyeglasses) to another image with another attribute (e.g., a face with eyeglasses). However, many attributes of interest for image domain translation are local in nature.

For example, translating a face image without eyeglasses to a face image with eyeglasses generally only involves changes to areas around the eye region. However, current GAN-based models are unable to explicitly focus on these localized regions during translation. This results in undesirable artefact in the generated output images.

Accordingly, it would be desirable to be able to provide a local visual attention-driven image translation mechanism that addresses at least some of the problems identified above.

SUMMARY

The aspects of the disclosed embodiments are directed to an apparatus or device, also referred to as an edge device, as a hardware-software solution that is configured to automatically transform the perceptual style of an image to reflect another perceptual style. This objective is solved by the subject matter of the independent claims. Further advantageous modifications can be found in the dependent claims.

According to a first aspect the above and further objects and advantages are obtained by an apparatus. In one embodiment, the apparatus includes a processor. The processor is configured to receive input image data corresponding to an output image of a first radiology scanner device, translate the input image data into a format corresponding to an output image of a second radiology scanner device and generate an output image corresponding to the translated input image data on a post processing imaging device associated with the first radiology scanner device. The aspects of the disclosed embodiments are configured to automatically transform a perceptual style of a radiology image generated by a first radiology imaging device into the perceptual style of a radiology image generated by a second radiology device. In this manner, the perceptual style of images resulting from the two devices will look similar.

In a possible implementation form of the apparatus, translating the input image data comprises in a first training phase, training a discriminator of a Generative Adversarial Network (GAN) to classify between images of a first domain and images of a second domain and generate a target attention image map using a prediction of the discriminator trained in the first phase. In a second training phase, the discriminator is trained with three input images. An input image corresponding to an image from the first domain, a synthesized image corresponding to the second domain generated by the generator of the GAN, and a set of real images corresponding to real images of the second domain. A degree of similarity between synthesized image and the set of real images is determined. A degree of dissimilarity between input image and the set of real images is determined. An attention map is generated based on the determined similarity between the synthesized image and the set of real images and the determined dissimilarity between the input image and the set of real images. A degree of similarity is determined between the attention map generated in the first training phase and the target attention image map generated in the second training phase. The GAN is trained using the determined degree of similarity between the attention map generated in the first training phase and the target attention map generated in the second training phase.

In a possible implementation form of the apparatus the first domain is the first radiology scanner device and the second domain is the second radiology scanner device. The apparatus can transform medical images from a new scanner to look like the images came from a scanner of another vendor a hospital might previously be used to.

In a possible implementation form of the apparatus, the first radiology scanner device comprises a first type of scanner device associated with a first vendor and the second radiology scanner device comprises the first type of scanner device associated with a second vendor. The aspects of the disclosed embodiments are configured to translate the output images of the scanner associated with the first vendor to look like the images from the scanner associated with the second vendor.

In a possible implementation form of the apparatus, the input is an image or video sequence.

In a possible implementation form of the apparatus the processor is configured to translate the input by modifying the format of the output of the first radiology scanner device to correspond to a perceptual style of the output of the second radiology scanner device.

In a possible implementation form of the apparatus, the processor is configured to use a machine learning model to translate the input into the format corresponding to the output of the second radiology scanner device.

In a possible implementation form of the apparatus, the processor is further configured to interpret a control variable that identifies how to translate the input image. The apparatus takes an image as an input and a control variable. The control variable tells the processor which attribute to change/translate in the image, and how much to change the image.

In a possible implementation form of the apparatus, the apparatus further comprises a controller. The controller is configured to adjust a degree of translation of the input image.

In a possible implementation form of the apparatus, the controller is configured to manually adjust the degree of translation of the input image. In one embodiment, a manually adjusted control, such as a knob, can be used to vary an amount of change in the image.

In a possible implementation form of the apparatus, the input is a medical image.

In a possible implementation form of the apparatus, the image of the first domain is a medical image generated by the first radiology scanner device and the image of the second domain is a medical image generated by the second radiology scanner device.

In a possible implementation form of the apparatus, the apparatus takes an image or a video sequence as input and produces another image or video sequence as output.

In a possible implementation form of the apparatus, an immediate application is in transforming medical images (CT, MR, XR etc) from a new scanner to look like it came from a scanner of another vendor a hospital might previously be used to.

In a possible implementation form of the apparatus, the apparatus can be used in conjunction with any modality (CT, MR, XR) of scanners from any existing vendor.

In a possible implementation form of the apparatus, the apparatus can be deployed either on the edge (e.g., processing on-board the scanner compute resources) or as a server-based application (where the apparatus can be connected to the scanners by means of wired or wireless connectivity).

In a possible implementation form of the apparatus, the apparatus can be used with multiple scanners at the same time (e.g., CT and MR simultaneously) by simply adding the modality-specific machine learning model capability to the apparatus. This way, the apparatus is modular and its capability can be easily increased/improved (e.g., add more modalities) easily by adding more compute units to the system, with each compute unit having the modality-specific machine learning models.

In a possible implementation form of the apparatus, the image or video sequences can be from any sensor (e.g., RGB, depth, thermal, RGB-depth, RGB-thermal etc.) or from any medical imaging modality (e.g., CT, MR, XR etc).

In a possible implementation form of the apparatus, the input/output relationship of the apparatus is specified by the machine learning model that processes the input data and produces the output data.

In a possible implementation form of the apparatus, the machine learning model is trained to translate the input image/video to an output image/video and the desired translation can be controlled by the user by means of a controllable knob, which can be implemented in a software-only, hardware-only, or a mixed-software-hardware fashion.

According to a second aspect the above and further objects and advantages are obtained by a method. In one embodiment the method includes receiving as input image data, output image data of a first radiology scanner device, translating the input image data into a format corresponding to output image data of a second radiology scanner device and generating an output image corresponding to the translated input image on a post processing imaging device associated with the first radiology scanner device.

In a possible implementation form of the method, translating the input image comprises in a first training phase, training a discriminator of a Generative Adversarial Network (GAN) to classify between images of a first domain and images of a second domain, generating a target attention image map using a prediction of the discriminator trained in the first phase, and in a second training phase, training the discriminator with an input image (A) corresponding to an image from the first domain, a synthesized image (B) corresponding to the second domain generated by the generator of the GAN, and a set of images (C) corresponding to real images of the second domain, determining a degree of similarity between images (B) and (C), determining a degree of dissimilarity between images (A) and (C), generating an attention map based on the determined similarity between images (B) and (C) and the determined dissimilarity between (A) and (C), determining a degree of similarity between the attention map generated in the first training phase and the target attention image map generated in the second training phase, and training the GAN using the determined degree of similarity between the attention map generated in the first training phase and the target attention map generated in the second training phase.

According to a third aspect the above and further objectives and advantages are obtained by a computer program product. In one embodiment, the computer program product includes a non-transitory computer readable media having stored thereon program instructions that when executed by a processor causes the processor to perform the method according to any one of the possible implementation forms recited herein.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings, in which.

DETAILED DESCRIPTION OF THE DISCLOSED EMBODIMENTS

Figure 1:
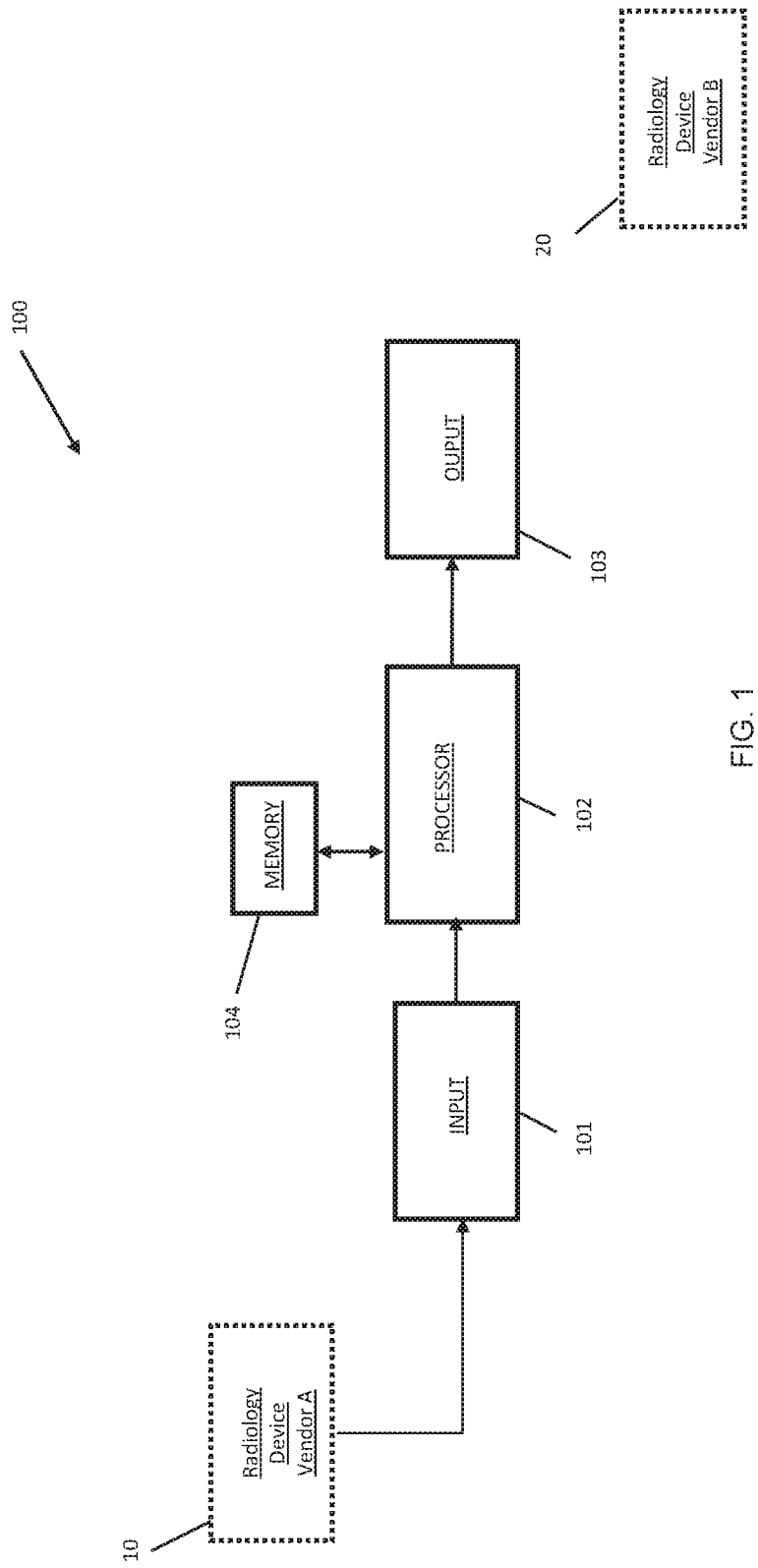
FIG. 1 illustrates a schematic block diagram of an exemplary apparatus incorporating aspects of the disclosed embodiments.

Referring to FIG. 1, a schematic block diagram of an exemplary apparatus 100 incorporating aspects of the disclosed embodiments is illustrated. The apparatus 100 is configured to receive input image data from a domain such as a radiology imaging device and transform the perceptual style of the image to correspond to a style of another domain, such as a radiology imaging device that is manufactured by a different vendor. The aspects of the disclosed embodiments are directed to translating images from one domain to another domain by automatically determining visual attention from machine learning models for image domain translation. For example, medical images from a new scanner can be transformed to look as if they from a scanner of another vendor.

As is illustrated in FIG. 1, the apparatus 100, also referred to as a device herein, includes at least one processor 102 and a memory 104. The processor 102 is configured to automatically transform the perceptual style of the input image. In one embodiment, the memory 104 is configured to store one or more programs which are executable by the processor 102. The at least one processor 102 and memory 104 can form or be part of a neural network. In one embodiment, the apparatus 100 can be referred to as an image domain translation Generative Adversarial Network (GAN).

As shown in FIG. 1, the processor 102 is configured to receive at least one input 101. In the example of FIG. 1, the input 101 generally comprises image data received from or generated by a first radiology imaging device 10. The term "image data" as is used herein generally refers to an input signal from one of a plurality of different types of radiology scanner devices, such as a medical scanner or portable medical scanner. For purposes of the examples herein, a radiology scanner device will be referred to. The aspects of the disclosed embodiments are not intended to be limited by the particular type of radiology or medical scanner device. In one embodiment, the input 101 generally comprises raw image data from a radiology scanner device.

Although the input 101 is generally referred to herein as image data, in one embodiment, the input 101 comprises a device including a processor, that is configured to receive image data generated by the first radiology scanner device 10 and provide that image data as an input to the processor 102.

As will be further described herein, the processor 102 is configured to translate a format or perceptual style of the image data of the input 101 into a format or perceptual style that corresponds to a perceptual style of a second domain, such as a second radiology scanner device 20, which is shown in Figure merely for illustrative purposes. The output 103 is the translated image data or a device that is configured to receive the translated image data from the processor 102 and provide that data to a post processing radiology imaging device. Generally, the first radiology scanner device will be produced or manufactured by a first vendor. The second radiology scanner device will be a type of device similar to and configured to function in the same or similar manner as the first radiology scanner device, but is produced or manufactured by a second vendor. Typically, the perceptual style of images generated by devices produced by different vendors will not be the same. While different vendors are referred to herein, the aspects of the disclosed embodiments are not so limited. In alternate embodiments, the apparatus 100 can be implemented in any environment where it is desired to match the perceptual style of an image or set of images, to the perceptual style of another set of images.

The apparatus 100 of the disclosed embodiments is configured to perform perceptual image style transfer for clinical applications. A machine learning model is trained to translate the input image data to the output image data. Generative Adversarial Networks (GANS) are used in training models that translate an image with one attribute into an image with another attribute. According to the aspects of the disclosed embodiments, a two-phase training approach is provided that introduces an additional learning objective during training of the GAN.

The aspects of the disclosed embodiments provide an additional learning objective that is used to train the GAN-based machine learning model to focus on the regions of interest, or important regions, rather than just the entirety of the image. This provides improvements in the quality of the transformed images.

During the first phase of the training of the GAN, the discriminator is trained to distinguish between the real images and the synthesized images. A target attention map is generated using the discriminator prediction.

In the second training phase, visual attention is an explicit part of the training process. An attention map is computed directly from the feature space that is learned by the discriminator. By enforcing consistency between the attention map of the synthesized image with eyeglasses and the ideal attention map, the aspects of the disclosed embodiments train the image domain translation GAN with both its traditional learning objectives and an attention consistency learning objective.

For purposes of the description and examples herein, the aspects of the disclosed embodiments will be described with respect to face images without eyeglasses and face images with eyeglass. The real image, or the image produced in the first domain will be a face image without eyeglasses. The desired image, or image corresponding to the second domain, is a face image with sunglasses. In these examples, the first domain is a first radiology scanner or imaging device produced by vendor A and the second domain is a second radiology scanner or imaging device produced by vendor B. The attribute or perceptual style in these examples in without eyeglasses and with eyeglasses.

The apparatus 100 in these examples is configured to transform or change the input image data 101 from the first radiology scanner device 10, representing the image of the face without eyeglasses, into an output 103, that is a face image with eyeglasses. In this manner, the perceptual style of the images of the second radiology scanner device 20, face images with eyeglasses, is maintained.

It will be understood that although the description herein related to maintaining a perceptual style of "with eyeglasses", the aspects of the disclosed embodiments are not so limited. In alternate embodiments, the desired perceptual style could be "without eyeglasses." In such a case, the training data and inputs would be modified accordingly. It will be understood that the aspects of the disclosed embodiments can be modified to address any desired, or even undesired, perceptual style or attribute. The aspects of the disclosed embodiments are directed to any implementation where it is desired to translate or change an image based on a control variable, where the control variable is configured to direct the apparatus 100 in how to translate the image, meaning which attribute(s) of the image to change/translate.

The apparatus 100 of the disclosed embodiments is configured to generate model visual attention from a GAN and then use this visual attention to further bootstrap the training of the GAN in order to perform perceptual image style transfer to generate as the output 103, an image with eyeglasses.

Figure 2:
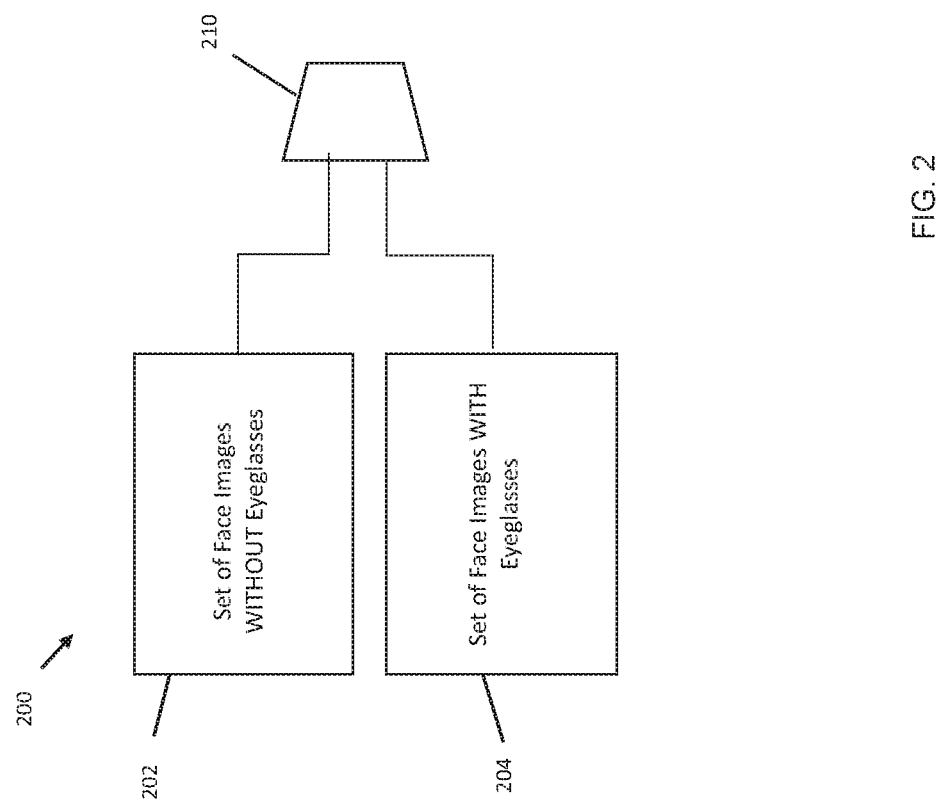
FIG. 2 illustrates an exemplary process flow incorporating aspects of the disclosed embodiments.
Figure 3:
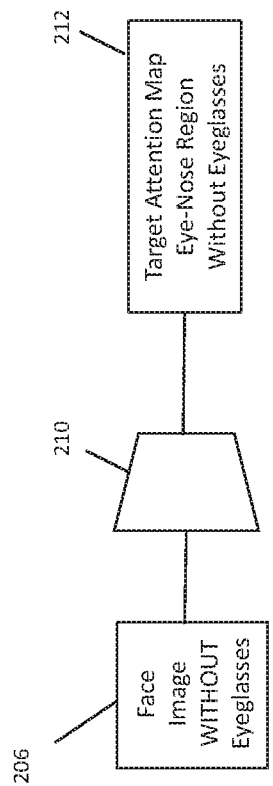
FIG. 3 illustrates an exemplary process flow incorporating aspects of the disclosed embodiments.

Referring to FIGS. 2 and 3, the aspects of the disclosed embodiments include two training phases. Referring to FIG. 2, in a first training phase 200, the discriminator 210 is trained to distinguish or discriminate between images from two different domains. In the example of FIG. 2, a first set of images 202 will include images with a one attribute, such as images "without eyeglasses." The second set of images 204 will include images with another attribute, which in this example is face images "with eyeglasses." The discriminator 210 in this example is trained to distinguish images "with eyeglasses" from images "without eyeglasses."

Figure 4:
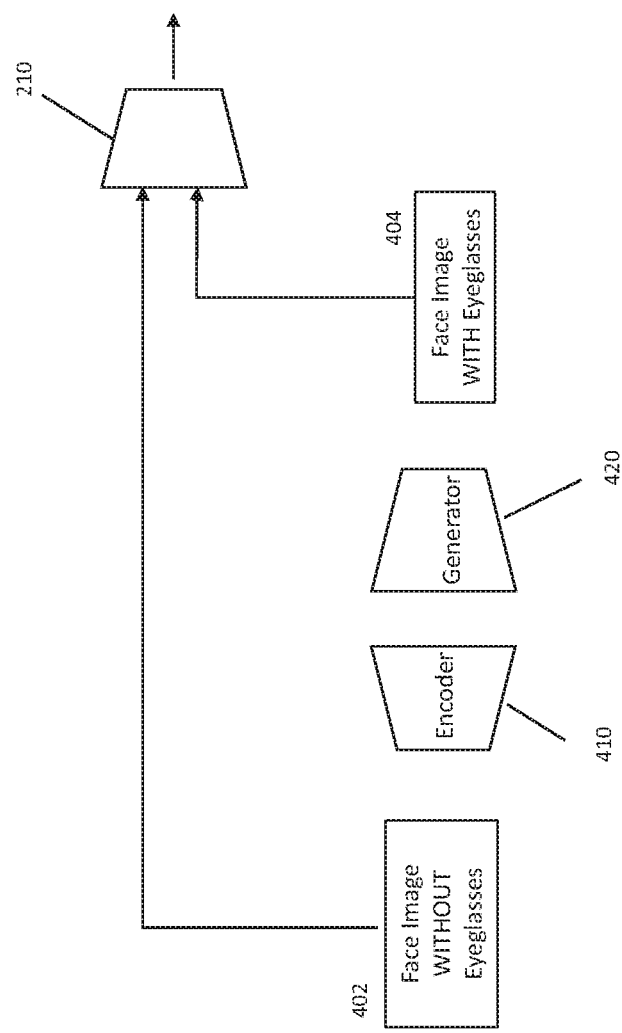
FIG. 4 illustrates an exemplary process flow incorporating aspects of the disclosed embodiments.

Once the discriminator 210 of FIG. 2 is trained, the generator of the GAN is configured to generate an image that cannot be disambiguated by the discriminator 210, as illustrated for example in FIG. 4. This can be understood to be the Nash equilibrium state. The generator 420 of the GAN is configured to generate or synthesize face images of people with eyeglasses, or in the contexts of attributes, an image with the desired perceptual style.

The aspects of the disclosed embodiments add locality to the framework of training the GAN. The training of the discriminator 210 in phase 1 is focused on the image as a whole. In the example of a face with eyeglasses, the attention is on the face as a whole and not just the areas or regions of the face where the eyeglasses would be located. The aspects of the disclosed embodiments focus the attention on the important regions, or regions that matter with respect to the desired perceptual style, such as "with eyeglasses" rather than "without eyeglasses."

As illustrated in FIG. 3, a target (visual) attention map 212 is computed using a prediction 206 of the discriminator 210. In this example, the prediction 206 is a face image without eyeglasses. The target attention map 212 identifies the ideal local regions. In this example, these ideal local regions are areas around the eyes and nose, where the glasses would be located. These ideal local regions from the target attention map 212 are then used to further train the GAN in the second phase of training, as is described below. Rather, than a global approach, the GAN of the disclosed embodiments is trained to look at only those regions that matter, referred to as the "important local regions."

As will be described below, during the second phase of the training of the GAN according to the aspects of the disclosed embodiments, the important local regions are generated. The process of generation of important local regions is guided by what is known about the ideal local region, which was determined in the target attention map 212 in the first training phase. In the example of FIG. 3, the target visual attention map 212 is configured to represent the localized area of changes around the eye region.

With respect to the exemplary attribute of "with eyeglasses", as the training of the GAN begins in the second training phase, it can be expected that since the model is not trained yet, it is likely that local regions will be produced that are not perfectly around the eye regions of the face. However, in one embodiment, a constraint or learning objective is imposed during this second training phase, which ensures that the local regions that are produced over time match the target attention map generated in the first training phase. In this manner, the aspects of the disclosed embodiments ensure that during training, the model is focused on the correct local regions, which for purposes of these examples is the region around the eyes where the eyeglasses would typically be disposed.

In the example of FIG. 4, after the first training phase, the generator 420 of the GAN is configured or trained to produce a synthetic face image 404 of a face with eyeglasses based on an input image 402, also referred to the real input image, of a face without eyeglasses. FIG. 4 illustrates how the generator 420 produces synthesized images 404 during training, which are face images with eyeglasses. In this example, the encoder 410 produces the feature vector of the input 402, the face image without glasses, which is used by the generator or decoder 420 to generate the synthesized image 404, the face image with glasses. The discriminator 210 in this example is distinguishing between the input image 404 and the synthesized image 402.

Figure 5:
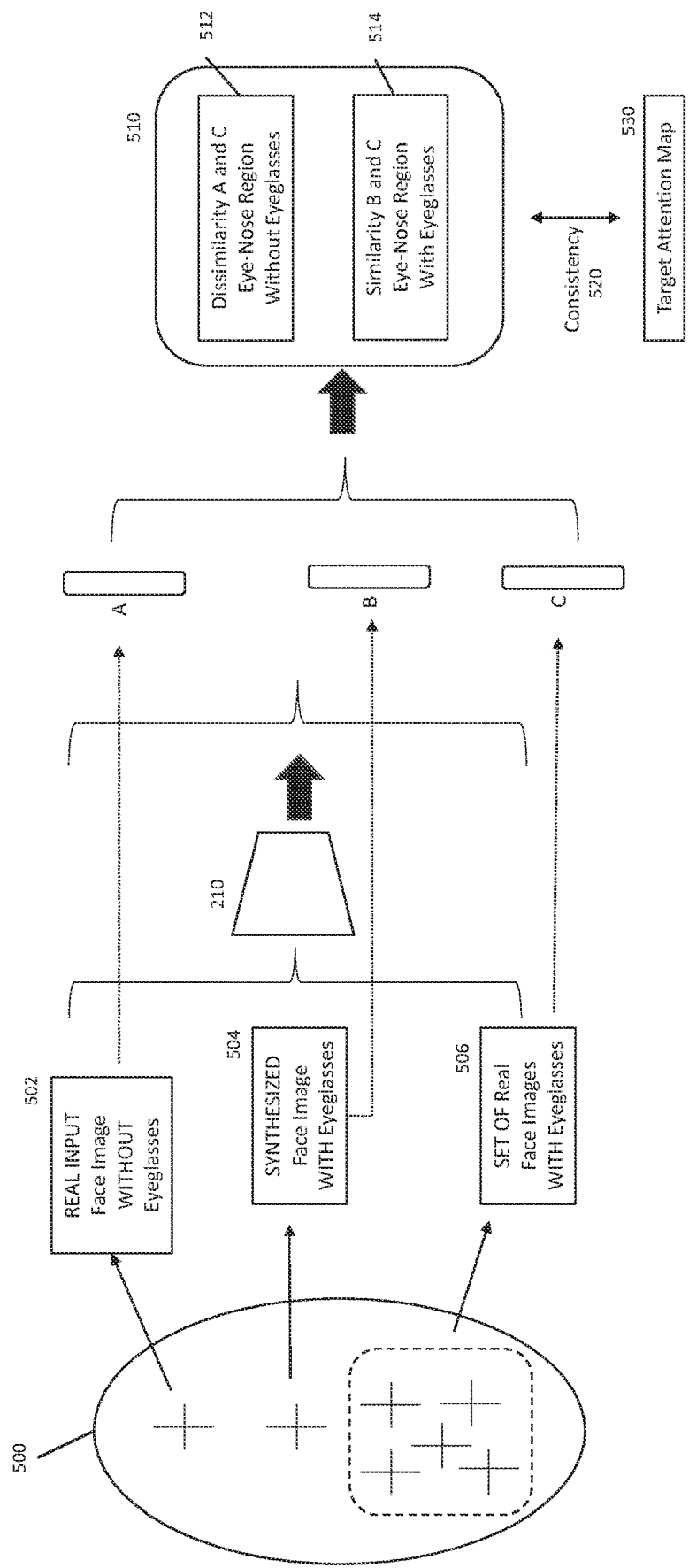
FIG. 5 illustrates an exemplary process flow incorporating aspects of the disclosed embodiments.

In the second training phase, the image domain translation GAN (e.g. CycleGAN or related models) is trained with visual attention being an explicit part of the training process. Referring to FIG. 5, the aspects of the disclosed embodiments compute attention maps directly from the feature space 500 learned by the discriminator 210.

In one embodiment, the representation or feature space 500 is used to determine the local regions that are important or of interest. In these examples, the local regions generally correspond to the regions of the desired perceptual style or attributes. The feature vectors of the inputs that represent the representation space 500 are used to generate an equivalent attention image 530, like the target attention map 212 generated in the first training phase. It is desired that the attention map 530 generated during this second training phase is substantially the same as or consistent with the target attention map 212 generated during the first training phase. That is the constraint that is being enforced.

Figure 6:
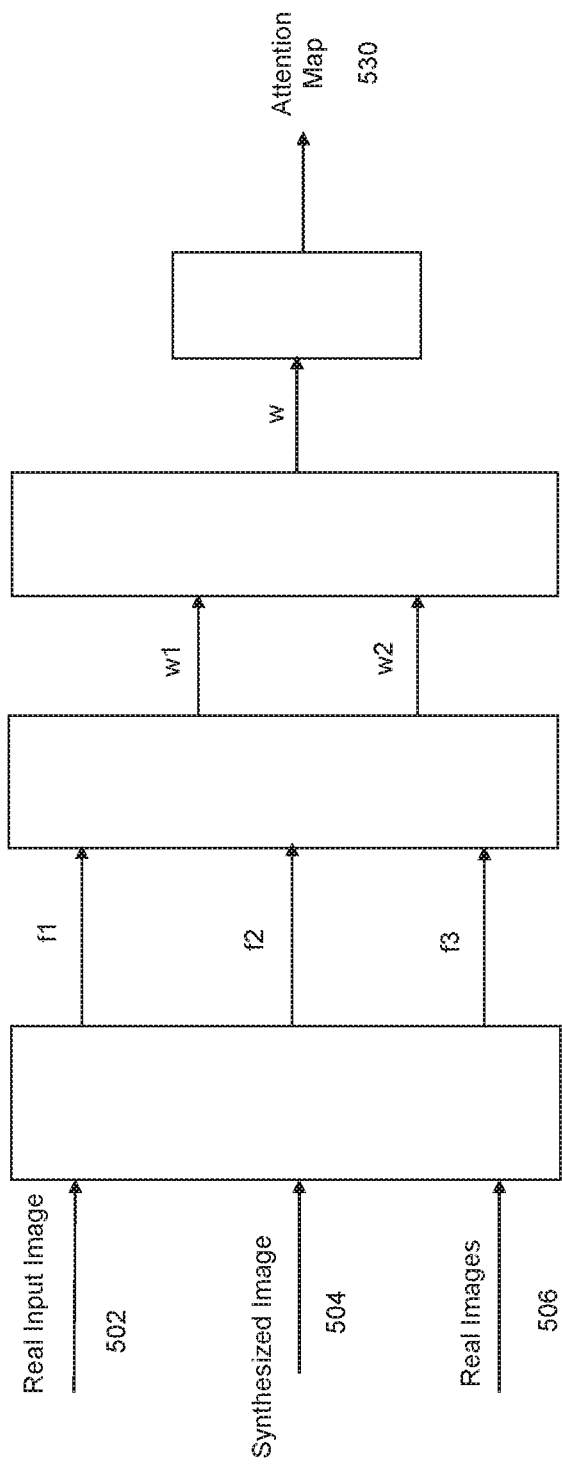
FIG. 6 illustrates an exemplary process flow incorporating aspects of the disclosed embodiments.

Referring to FIGS. 5 and 6, in this example, three entities from the feature space 500 are passed or input to the discriminator 210. The three entities include the real input image 502, which is the face image without eyeglasses; the synthesized image 504 from the generator 420; and a set 506 of all real images which have the same attribute as that being synthesized, which in this example is a set of face images with eyeglasses. This set 506 of real face images with eyeglasses is a set that is available or known during training.

As illustrated in FIG. 5, the inputs to the discriminator 210 are the images 502, 504 and 506. A, B and C shown in FIG. 5 are the feature vectors that correspond to the images 502, 504 and 506, respectively, that are obtained from one of the feature layers of the discriminator 210. As will be understood, the discriminator 210 of the disclosed embodiments is a neural network with a number of different layers. By passing the image entities 502, 504, 506 through the neural network, a corresponding feature vector A, B and C, can be obtained for each. The feature vectors A, B and C and comprise any suitably dimensioned feature vector. For example, the feature vectors A, B and C can comprise 10-dimensonal feature vectors or 20-dimensional feature vectors. The aspects of the disclosed embodiments are not intended to be limited by the particular size or type of feature vector.

With respect to the set of images 506, in one embodiment, each image from the set of images 506 is passed through the neural network to produce a set of feature vectors. For example, if there are five (5) images in the set of images 506, five feature vectors will be produced. In one embodiment, a suitable aggregation algorithm can be used to generate the feature vector C from the set of feature vectors that is produced.

In one embodiment, the effectiveness or accuracy of the current state of the generator 420 in generating synthesized images is determined by taking the three entities 502, 504 and 506 as the inputs to the discriminator 210, as is shown in FIG. 5. As will be understood, it is desired that a synthesized eyeglass image looks as close to a real eyeglass image as possible, while still distinguishing or differentiating from an image without eyeglasses. It is desired to be able to capture the local differences between the image with eyeglasses and the image without eyeglasses.

Referring again to FIG. 5, the input A is the feature vector representing the face image without eyeglasses, input B is the feature vector of the synthesized face image with eyeglasses and input C is the feature vector representing the set of real face images with eyeglasses. Image 502, the real image without eyeglasses, and image 506, the real image with eyeglasses, will be dissimilar because of the eyeglasses. The dissimilarity is the eyeglass region. Image 504 is the synthesized image from the generator 420 of FIG. 4.

It will be understood that it is desired that image 504, the synthesized face image with eyeglasses be close or similar to image 506, the set of real face images with eyeglasses. It is also desired to capture the differences between image 502, the real face image without eyeglasses and image 504, the synthesized face image with eyeglasses. The important differences or areas on interest is the eyeglass region of the face, also referred to herein as the local region. The feature vectors A, B and C will be processed to assess and determine the differences. Existing methods can applied to the feature vectors A, B and C determine the measure of similarity and dissimilarity and identify the feature dimensions that are important. The differences will be highlighted in the resulting attention maps 510.

For example, as shown in FIG. 5, the target attention map 512 highlights the differences between feature vectors A and C, while the target attention map 514 highlights the differences between feature vectors A and B. Using existing methods, the dimensions in the feature vectors that are important can be determined to satisfy these conditions. Once the dimensions are identified, the attention map 530 can be produced in a manner similar to the production of the attention map 212 is the first phase.

Once the attention map 530 is produced, a similarity between the attention map 530 and the attention map 212 of the first phase is measured. The similarity measure is then used to train the GAN.

Existing methods to train GANs have a learning objective, which can be referred to as L1. The aspects of the disclosed embodiments add an extra term to this learning objective L1, referred to herein as L2, to produce a training objective of L1+L2 in phase two of the training. L2 is the measure of similarity between the attention map 212 produced in phase one and the attention map 530 produced in phase two. Once the GAN is trained and converged based on L1+L2, the generator of the GAN can be implemented in the apparatus 100 shown in FIG. 1.

The measurement of the similarity of the target attention map 212 generated during the first phase with the target attention map 530 generated during the second phase can be achieved using a variety of different machine learning techniques. Examples include, but are not limited to, Euclidean objective, where the distance between two images is measured, or other such suitable similarity function. Once the level of similarity is determined, the training or learning process is penalized based on the quantified similarity. This is the consistency 520 of FIG. 5.

FIG. 6 is a schematic block diagram of a process flow incorporating aspects of the disclosed embodiments. In this example, the feature vectors f1, f2 and f3 correspond to the real input image 502, the synthesized image input 504 and the set of real images input 506, respectively. The feature vectors f1, f2, and f3 are used to determine the current state of the discriminator 210 and generator 420.

As shown in FIG. 6, two difference vectors w1, w2 are formed from the processing of the feature vectors f1, f2 and f3, using existing similarity methods. In this example, the first difference vector is w1=abs(f1−f2). The second difference vector is w2=abs(f1−f3). A single weight vector w is constructed by computing the element-wise product of w1 and w2. In this manner, dimensions in the feature space of the discriminator 210 are identified that contribute to the final decision of the discriminator 210. With the single weight vector w, the dot product with the feature vector of the synthesized image can be computed to obtain the corresponding attention map 530 illustrated in FIG. 5.

The aspects of the disclosed embodiments enforce attention consistency (i.e., same attention) between the attention map 530 of the synthesized image and the corresponding ideal attention map 212 and backpropagate the corresponding gradients to both the discriminator 210 as well as the generator 420. Consequently, the image domain translation GAN will be trained with both its traditional learning objectives L1 as well the attention consistency learning objective L2 of the disclosed embodiments.

The aspects of the disclosed embodiments are not restricted to any specific task or GAN model architecture. The visual attention model of the disclosed embodiments is flexible and scalable, and can be used in conjunction with any existing off-the-shelf GAN model, thereby increasing its utility in being used a drop-in tool to visually explain GANs by means of the resulting visual attention.

Figure 7:
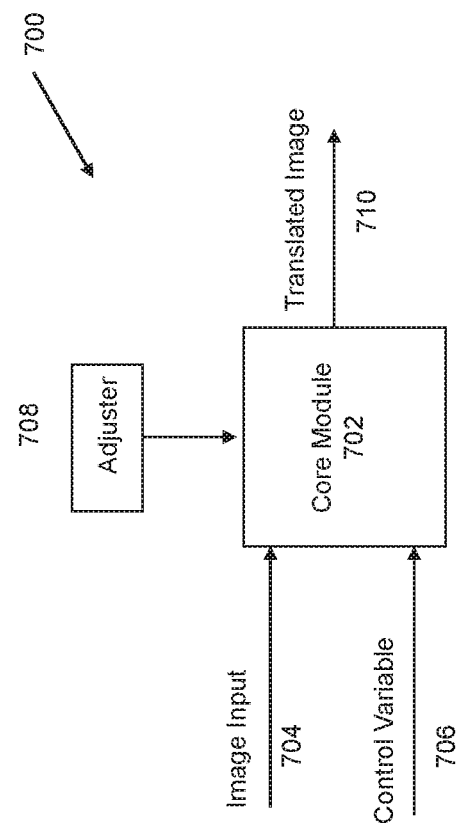
FIG. 7 illustrates a block diagram of an exemplary apparatus incorporating aspects of the disclosed embodiments.

Referring to FIG. 7, in one embodiment, a system 700 configured to perform perceptual image style transfer comprises a core module 702 comprising the image translation GAN trained according to the method above. In one embodiment, the core module 702 comprises or includes the processor 102 described with respect to FIG. 1. The system 700 takes an image as input 704 as well as a control variable 706. The control variable 706 tells the system 700 how to translate the image (i.e., which attribute to change/translate in the input image). In one embodiment, the system 700 includes a user-controllable switching device or controller 708, also referred to as a control knob, that can be varied to adjust the level of translation in the output image 710 (i.e., how much change in the image). The controller 708 can be implemented in a software-only, hardware-only, or a mixed-software-hardware fashion.

The system 700 can be implemented in clinical scenarios where clinicians are historically used to a certain kind of images from their existing scanners. To make them more comfortable adopting a new scanner, the system 700 can be used to translate the output images to "look like" images from their existing scanners. This will help increase the acceptability of the new scanners since the clinicians will be more comfortable with the resulting images.

Figure 8:
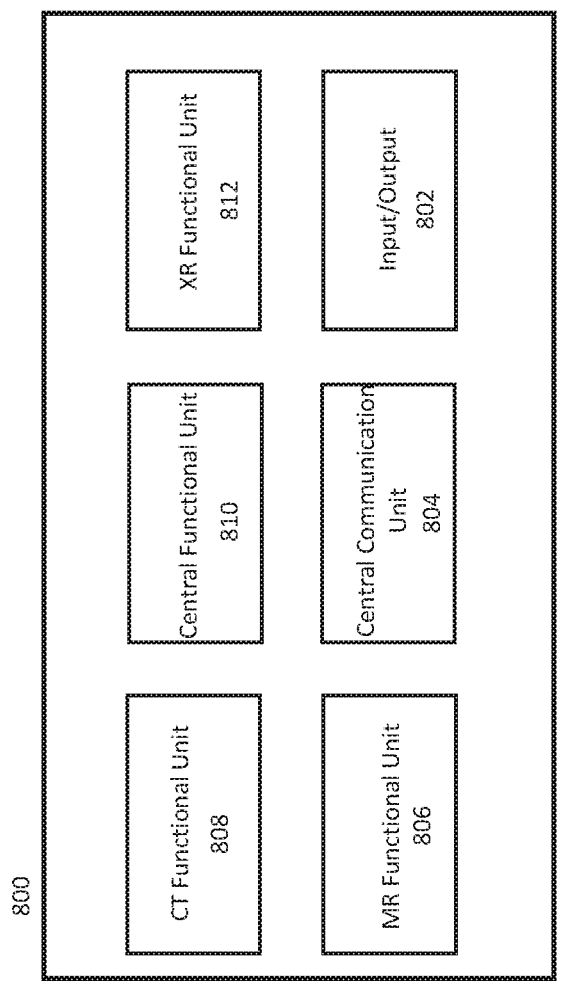
FIG. 8 illustrates a block diagram of an exemplary apparatus incorporating aspects of the disclosed embodiments.

FIG. 8 illustrates a block diagram of an apparatus 800 incorporating aspects of the disclosed embodiments. The apparatus 800 is configured to perform perceptual image style transfer as is described herein. The system or apparatus 800 is configured to be used with multiple scanners at the same time, by simply adding the modality-specific machine learning model capability to the system. The examples in FIG. 8 include, but are not limited to, magnetic resonance (MR) provided by MR functional unit 806; computed tomography (CT) provided by CT functional unit 808; and X-ray (XR) provided by XR functional Unit 812. In this manner, the system 800 is modular and its capability can be easily increased/improved by adding more modalities in the form of functional or computing units to the system 800, with each computing unit having the modality-specific machine learning models.

In this example, the apparatus 800 also includes an input/output module 802. The input/output module 802 is configured to receive data from radiology scanner of vendor X and translate the received data to look like an output image from a radiology scanner of vendor Y, as is generally described herein.

The central communication unit 804 is configured to enable communication between the different devices and components that are generally described herein. In one embodiment, the central communication unit 804 can include one or more communication networks or modules to enable communication and the transfer of information to and from the apparatus 100. The communication network may be a wired or wireless communication network. Examples of the communication network may include, but are not limited to, a Wireless Fidelity (Wi-Fi) network, a Local Area Network (LAN), a wireless personal area network (WPAN), a Wireless Local Area Network (WLAN), a wireless wide area network (WWAN), a cloud network, a Long Term Evolution (LTE) network, a plain old telephone service (POTS), a Metropolitan Area Network (MAN), and/or the Internet. Exemplary communication protocols can include wired and wireless communication protocols, such as but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, Long Term Evolution (LTE), Light Fidelity (Li-Fi), and/or other cellular communication protocols or Bluetooth (BT) communication protocols, including variants thereof.

The Central Function Unit 810 is configured for functional processing that is common to all modalities. For instance, depending on the application, there can be some common processing across multiple modalities that the Central Function Unit 810 is configured to perform. This can be in addition to more modality-specific processing that is handled by the respective functional units.

Referring again to FIG. 1, examples of the processor 102 includes, but are not limited to, a microprocessor, a microcontroller, a complex instruction set computing (CISC) microprocessor, a reduced instruction set (RISC) microprocessor, a very long instruction word (VLIW) microprocessor, or any other type of processing circuit. Optionally, the processor 102 may be one or more individual processors, processing devices and various elements associated with a processing device that may be shared by other processing devices. Additionally, the one or more individual processors, processing devices and elements are arranged in various architectures for responding to and processing the instructions that drive the apparatus 100.

The memory 104 can generally comprise suitable logic, circuitry, interfaces, and/or code that may be configured to store instructions executable by the processor 102. Exemplary implementations of the memory 104 may include, but are not limited to, Random Access Memory (RAM), Read Only Memory (ROM), Hard Disk Drive (HDD), Flash memory, and/or a Secure Digital (SD) card. A computer readable storage medium for providing a non-transient memory may include, but is not limited to, an electronic storage device, a magnetic storage device, an optical storage device, an electromagnetic storage device, a semiconductor storage device, or any suitable combination of the foregoing.

The aspects of the disclosed embodiments are configured to take an image or a video sequence as input and produces another image or video sequence as output. The image or video sequences can be from any sensor (e.g., RGB, depth, thermal, RGB-depth, RGB-thermal etc) or from any medical imaging modality (e.g., CT, MR, XR etc). An immediate application of the system or apparatus of the disclosed embodiments is in transforming medical images (CT, MR, XR etc.) from a new scanner to look like it came from a scanner of another vendor a hospital might previously be used to. The apparatus can be used in conjunction with any modality (CT, MR, XR) of scanners from any existing vendor.

The apparatus of the disclosed embodiments can be deployed either on the edge (e.g., processing on-board the scanner compute resources) or as a server-based application (where the system can be connected to the scanners by means of wired or wireless connectivity). The apparatus can also be used with multiple scanners at the same time (e.g., CT and MR simultaneously) by simply adding the modality-specific machine learning model capability to the system. This way, the apparatus is modular and its capability can be easily increased and improved easily by adding more computing units, with each computing unit having the modality-specific machine learning models.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. An apparatus comprising a processor, the processor configured to:
   receive input image data corresponding to output image data of a first radiology scanner device;
   translate the input image data into a format corresponding to output image data of a second radiology scanner device by:
      in a first training phase, training a discriminator of a Generative Adversarial Network (GAN) to classify between images of the first radiology scanner device and images of the second radiology scanner device;
      generating a target attention image map using a prediction of the discriminator trained in the first phase; and
      in a second training phase, training the discriminator with an input image corresponding to a real input image of the first radiology scanner device, a synthesized image generated by the generator of the GAN, and a set of images corresponding to real images of the second radiology scanner device;

determining a degree of similarity between the synthesized image and the set of real images;
determining a degree of dissimilarity between the real input image and the set of real images;
generating an attention map based on the determined similarity between the synthesized image and the set of real images and the determined dissimilarity between the real input image and the set of real images;
determining a degree of similarity between the target attention image map generated in the first training phase and the attention map generated in the second training phase; and
training the GAN using the determined degree of similarity; and
generate an output image corresponding to the translated input image data on a post processing imaging device associated with the first radiology scanner device.

2. The apparatus according to claim 1, wherein the apparatus is further configured to determine a feature vector corresponding to the real input image, a feature vector for the synthesized input image and a feature vector for the set of real images for generating the attention map in the second phase.

3. The apparatus according to claim 1, wherein the first radiology scanner device comprises a first type of scanner device associated with a first vendor and the second radiology scanner device comprises a second type of scanner device associated with a second vendor.

4. The apparatus according to claim 1, wherein the input is an image or video sequence.

5. The apparatus according to claim 1, wherein the processor is configured to translate the input by modifying the format of the output of the first radiology scanner device to correspond to a perceptual style of the second radiology scanner device.

6. The apparatus according to claim 1, wherein the processor is configured to use a machine learning model to translate the input image data into the format corresponding to the output of the second radiology scanner device.

7. The apparatus according to claim 1, further comprising a controller, the controller configured to adjust a degree of translation of the input image data.

8. The apparatus according to claim 1, wherein the controller is a manually adjusted control.

9. The apparatus according to claim 1 wherein the input image data is a medical image.

10. The apparatus according to claim 1, wherein the input image data of a first domain is a medical image generated by the first radiology scanner device and the output image data of a second domain is a medical image generated by the second radiology scanner device.

11. The apparatus according to claim 1, wherein the apparatus is implemented as an edge device in a radiology system.

12. A method comprising:
receiving input image data corresponding to output image data of a first radiology scanner device;
translating the input image data into a format corresponding to output image data of a second radiology scanner device by:
in a first training phase, training a discriminator of a Generative Adversarial Network (GAN) to classify between images of the first radiology scanner device and images of the second radiology scanner device;
generating a target attention image map using a prediction of the discriminator trained in the first phase; and
in a second training phase, training the discriminator with an input image corresponding to a real input image of the first radiology scanner device, a synthesized image generated by the generator of the GAN, and a set of images corresponding to real images of the second radiology scanner device;
determining a degree of similarity between the synthesized image and the set of real images;
determining a degree of dissimilarity between the real input image and the set of real images;
generating an attention map based on the determined similarity between the synthesized image and the set of real images and the determined dissimilarity between the real input image and the set of real images;
determining a degree of similarity between the target attention image map generated in the first training phase and the attention map generated in the second training phase; and
training the GAN using the determined degree of similarity; and
generating an output image corresponding to the translated input image data on a post processing imaging device associated with the first radiology scanner device.

13. The method according to claim 12, wherein the method further includes determining a feature vector corresponding to the real input image, a feature vector for the synthesized input image and a feature vector for the set of real images for generating the attention map in the second phase.

14. The method according to claim 12, wherein the first radiology scanner device comprises a first type of scanner device associated with a first vendor and the second radiology scanner device comprises a second type of scanner device associated with a second vendor.

15. The method according to claim 12, wherein a machine learning model is trained to translate the input image into the format corresponding to the output image data, and a degree of translation is controlled by a user control.

16. The method according to claim 12, wherein the input image data of a first domain is a medical image generated by the first radiology scanner device and the output image data of a second domain is a medical image generated by the second radiology scanner device.

17. A computer program product comprising non-transitory machine readable instructions, which when executed, are configured to carry out the method according to claim 12.

* * * * *